US00PP34462P3

(12) United States Plant Patent
Olesen

(10) Patent No.: US PP34,462 P3
(45) Date of Patent: Aug. 2, 2022

(54) MINIATURE ROSE PLANT NAMED 'POULPAR113'

(50) Latin Name: *Rosa hybrida*
Varietal Denomination: 'Poulpar113'

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 17/300,626

(22) Filed: Sep. 7, 2021

(65) Prior Publication Data

US 2022/0095506 P1 Mar. 24, 2022

(30) Foreign Application Priority Data

Sep. 21, 2020 (QZ) ..... PBR 2020/2248

(51) Int. Cl.
*A01H 5/02* (2018.01)
*A01H 6/74* (2018.01)

(52) U.S. Cl.
USPC ..... Plt./119
CPC ..... *A01H 6/749* (2018.05)

(58) Field of Classification Search
USPC ..... Plt./101, 116, 118, 119
See application file for complete search history.

*Primary Examiner* — Susan McCormick Ewoldt

(57) ABSTRACT

A new garden rose plant of the Miniature class which has abundant, yellow orange flowers and attractive foliage. This new and distinct variety has shown to be uniform and stable in the resulting generations from asexual propagation.

1 Drawing Sheet

Botanical designation: *Rosa hybrida.*
Variety denomination: 'Poulpar113 '.

This application claims priority to Plant Breeder's Rights Application Number 2020/2248, which was filed at the Community Plant Variety Rights Office in the European Union on Sep. 21, 2020, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2010 and the resulting seeds were planted in a controlled environment in Fredensborg, Denmark. The new variety, named 'Poulpar113', originated as a single seedling from the stated cross.

The new variety may be distinguished from its male pollen parent and female seed parent primarily by the following characteristics. The male pollen parent plant has light pink flowers while the new variety has yellow orange flowers. The female seed parent plant has light yellow flowers while the new variety has yellow orange flowers.

The objective of the hybridization of this rose variety was to create a new and distinct variety with unique qualities, such as:

1. Uniform and abundant yellow orange flowers;
2. Vigorous, but compact growth when propagated on its own roots;
3. Exceptional disease resistance.

This combination of qualities is not present in previously available commercial cultivars of this type, known to the inventor, and distinguish 'Poulpar113' from all other varieties of which we are aware.

As part of the rose development program, Mogens N. Olesen germinated the seeds from the aforementioned hybridization during winter of 2010 and conducted evaluations on the resulting seedlings in a controlled environment in Fredensborg, Denmark. 'Poulpar113' was selected in the spring of 2011 by the inventor as a single plant from the progeny of the aforementioned hybridization.

Asexual reproduction of 'Poulpar113' by rooted cuttings was first done by Mogens N. Olesen in the nursery in Fredensborg, Denmark in July, 2011. This initial and other subsequent asexual propagations conducted in controlled environments have demonstrated that the characteristics of 'Poulpar113' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulpar113'. Specifically illustrated in the drawing is an open flower viewed from above and the side, flower buds, leaves with juvenile coloration and mature coloration, bare stems, and detached flower petals revealing reproductive flower parts and receptacle. Plants shown are 4 months years of age.

DETAILED DESCRIPTION OF THE VARIETY

The following is a description of 'Poulpar113', as observed in its growth in a controlled environment greenhouse in Odense Denmark. Observed plants are 4 months old and were grown on their own roots in 19 cm containers. Color references are made using The Royal Horticultural Society (London, England) Colour Chart, 2001, except where common terms of color are used.

For a comparison, several physical characteristics of the rose variety 'Poulpar071', U.S. Plant Pat. No. 24,549 are compared to 'Poulpar113' in Chart 1.

CHART 1

| | 'Poulpar113' | 'Poulpar071' |
|---|---|---|
| Petal Count | 48 | 70 |
| Flower Diameter | 45 mm | 50 to 60 mm |
| General Tonality of Flower Color | Yellow-Orange Group 23B. Yellow-Orange Group 16B after flowers have fully matured | Orange Group 23B and Orange-Red Group N34C at middle zone |

FLOWER AND FLOWER BUD

Blooming habit: Continuous.

Flower bud:

*Size.*—Upon opening, 21 mm in length from base of receptacle to end of bud. Bud diameter is 10 mm.

*Bud form.*—Ovoid. Color: Yellow-Green Group 144A.

*Sepal inner surface.*—Color: Yellow-Green Group 146D. Surface: Lightly pubescent.

*Sepal outer surface.*—Color: Yellow-Green Group 144A. Some sepals exhibit streaks of Red Group 146D. Texture: Smooth.

*Sepal shape.*—Apex: Cirrhose. Base: Flat at union with receptacle.

*Sepal margin.*—Margins have weak foliaceous appendages on three of the five sepals.

*Sepal size.*—20 mm long, 8 mm wide.

*Receptacle.*—Texture: Smooth. Size: 4 mm in height, 5 mm wide. Color: Yellow-Green Group 144A. Shape: Funnel.

*Pedicel.*—Surface: Smooth. Length: 31 mm. Diameter: 3 mm on average. Color: Yellow-Green Group 144A. Strength: Strong.

*Peduncle.*—Length: 2 to 4 cm. Diameter: About 3.5 mm. Color: Yellow-Green Group 145A. Texture: Smooth.

Flower bud development: Flower buds are borne singly or in clusters of 3 flower buds per stem.

Flower bloom:

*Fragrance.*—Moderate floral scent.

*Duration.*—The blooms have a duration on the plant of approximately 21 days. Petals fall cleanly away from plant after flowers have fully matured.

*Size.*—Flower diameter is 45 mm when open. Flower depth is 20 mm.

*Flower shape.*—Rosette.

*Shape of flower, side view.*—The upper portion is convex. The lower portion is concave.

Petalage: Under normal conditions, flowers have about 48 petals.

General tonality of flower: Open flowers are Yellow-Orange Group 23B. Yellow-Orange Group 16B after flowers have fully matured.

Petal color:

*Upon opening, outer petals.*—Upper surface: Yellow-Orange Group 23B. At the basal zone Yellow Group 13A. Lower surface: Orange Group 25B shaded with Orange-Red Group 30C. Yellow Group 13C petal spot.

*Upon opening, inner petals.*—Upper surface: Yellow Group 13A shaded with Orange Group 24B. Lower surface: Orange Group 25A with intonations of Yellow-Orange Group 23B shaded. Petal spot Yellow Group 13C.

*After opening, outer and inner petals.*—Upper surface: Yellow-Orange Group 22B. At the basal zone Yellow Group 12A. Lower surface: Orange Group 24C. At the basal zone Yellow Group 13C.

Petals:

*Petal reflex.*—Strong.

*Margin.*—Entire and uniform. Moderate undulations.

*Shape.*—Broad and elliptic. Apex shape: Rounded. Base shape: Acute.

*Size.*—21 mm (l)×21 mm (w).

*Texture.*—Smooth.

*Thickness.*—Average.

Petaloids:

*Size.*—9 mm (l) by 8 mm (w).

*Quantity.*—About 11.

*Shape.*—Elliptical with an acute base and rounded apices.

*Color.*—The upper surface is Yellow Group 13A shaded with Orange Group 24B. Lower surface is Orange Group 25A with intonations of Yellow-Orange Group 23B shaded. Petaloid spot is Yellow Group 13C on lower side.

Reproductive flower parts:

*Pollen.*—None observed.

*Anthers.*—Size: 2 mm in length. Color: Yellow Group 12A. Quantity: 35 on average.

*Filaments.*—Color: Yellow Group 13C. Length: 4 mm.

*Pistils.*—Length: 5 mm. Quantity: 23 on average.

*Stigmas.*—Color: Greyed-Yellow Group 160.

*Styles.*—Color: Greyed-Yellow Group 160.

*Hips.*—None Observed.

PLANT

Plant growth: Upright, compact. Plants are 39 cm in height, and 35 cm wide.

Stems:

*Color of juvenile growth.*—Yellow-Green Group 144B.

*Color of mature growth.*—Yellow-Green Group 144A.

*Length.*—Canes are about 19 cm from the base of the plant to the flowering portion.

*Diameter.*—About 4 to 5 mm.

*Internodes.*—On mature canes about 25 mm between nodes.

*Surface texture.*—Young wood: Smooth. Older wood: Smooth.

Long prickles:

*Incidence.*—5 prickles per 10 cm of stem.

*Size.*—Average length of prickles on mature stems is 4 mm.

*Shape.*—Upper portion is linear. Lower portion is linear.

*Color.*—Juvenile prickles: Greyed-Yellow Group 160B. Mature prickles: Greyed-Yellow Group 160B.

Plant foliage:

*Compound leaf.*—106 mm (l)×70 (w).

*Quantity.*—3 to 4 leaves per 10 cm of stem on average.

*Leaf bearing angle to the stem.*—45 degrees.

*Color of juvenile foliage.*—Upper side: Yellow-Green Group 146B with intonations of Greyed-Purple Group N186C. Lower side: Yellow-Green Group 144B & Greyed-Purple Group 184A.

*Color of mature foliage*.—Upper side: Yellow-Green Group 147A. Lower side: Yellow-Green Group 147B.

Plant leaves and leaflets:

*Stipules*.—Size: 6 mm long, mm wide. Quantity: 2 per compound leaf. Shape: Linear, slightly broad based with outward extending apices. Margins: Finely serrated. Color: Yellow-Green Group 144A.

*Petiole*.—Length: 20 mm. Diameter: 2 mm. Upper surface color: Yellow-Green Group 144A. Lower surface color: Yellow-Green Group 144A.

*Rachis*.—Length: 40 mm. Upper surface color: Yellow-Green Group 144A. Lower surface color: Yellow-Green Group 144A.

*Leaflet*.—Quantity: Normally 5 leaflets. Margins: Serrated. Size: Terminal leaflets are about 45 mm long, 27 mm wide. Shape: Generally elliptical. Base: Rounded. Apex: Acute to mucronate. Texture: Smooth. Thickness: Average. Arrangement: Odd pinnate. Venation: Reticulate. Glossiness: Not glossy.

Disease resistance: Above average resistance to powdery mildew *Sphaerotheca pannosa* var. *rosae,* downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Miniature rose class named 'Poulpar113', substantially as illustrated and described herein, due to its abundant yellow orange flowers, disease resistance, and extended period of bloom.

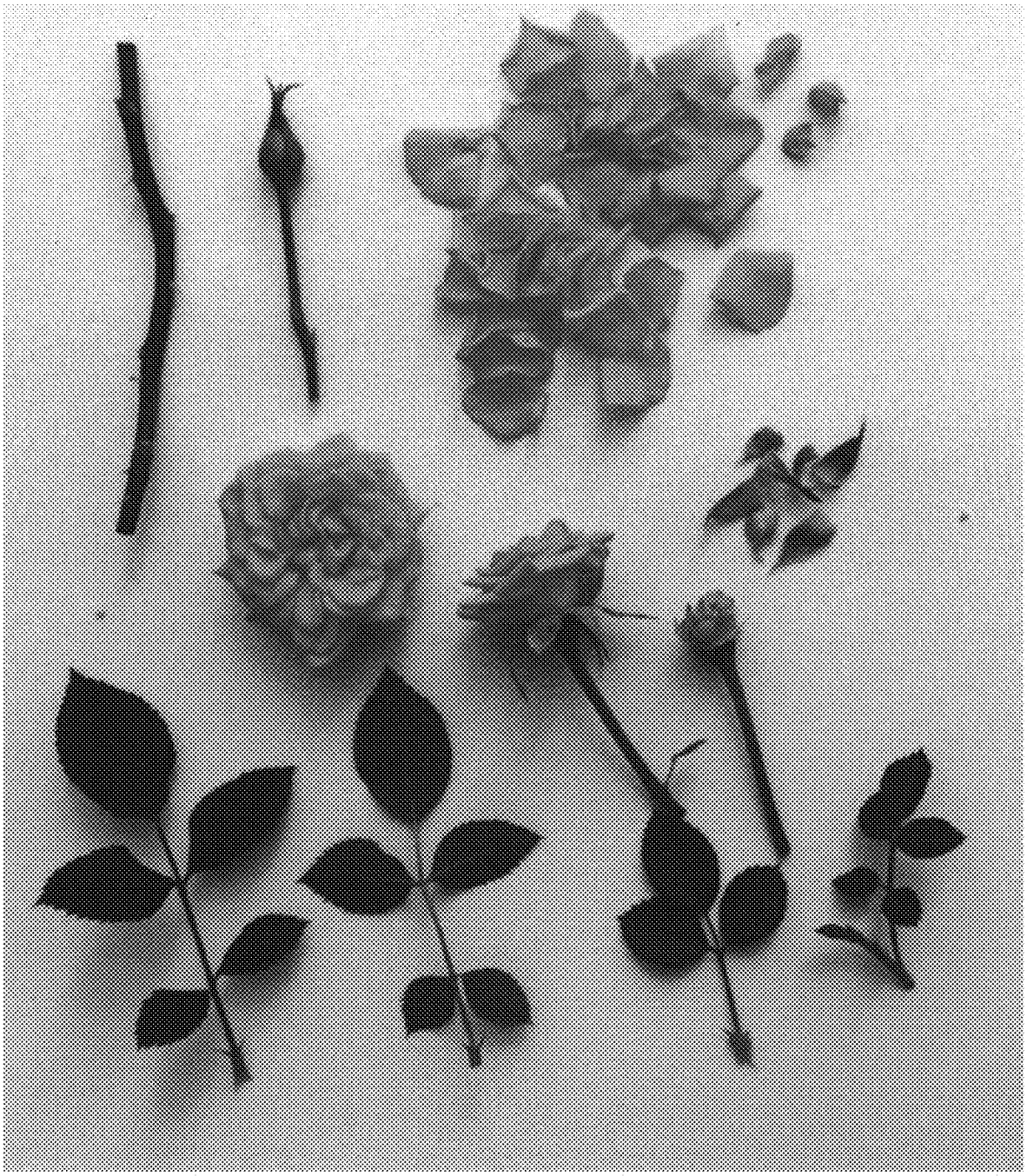

* * * * *